US005588960A

United States Patent [19]
Edwards et al.

[11] Patent Number: 5,588,960
[45] Date of Patent: Dec. 31, 1996

[54] TRANSURETHRAL NEEDLE DELIVERY DEVICE WITH CYSTOSCOPE AND METHOD FOR TREATMENT OF URINARY INCONTINENCE

[75] Inventors: Stuart D. Edwards, Los Altos; Ronald G. Lax, Grass Valley; Hugh R. Sharkey, Redwood City, all of Calif.

[73] Assignee: Vidamed, Inc., Menlo Park, Calif.

[21] Appl. No.: 349,064

[22] Filed: Dec. 1, 1994

[51] Int. Cl.⁶ .................................................. A61B 17/39
[52] U.S. Cl. ............................................................ 604/20
[58] Field of Search ................................. 604/19–22, 53, 604/164, 280; 601/2; 606/39, 45, 32, 47, 48; 607/96, 113, 115, 116, 138, 156

[56] References Cited

U.S. PATENT DOCUMENTS

| | | |
|---|---|---|
| 4,019,498 | 4/1977 | Hawtrey et al. . |
| 4,457,299 | 7/1984 | Cornwell . |
| 4,580,578 | 4/1986 | Barsom . |
| 4,857,041 | 8/1989 | Annis et al. . |
| 4,950,267 | 8/1990 | Ishihara et al. ........................ 606/12 |
| 5,003,991 | 4/1991 | Takayama et al. ..................... 128/784 |
| 5,149,329 | 9/1992 | Richardson . |
| 5,304,147 | 4/1994 | Johnson et al. . |
| 5,324,775 | 6/1994 | Rhee et al. . |
| 5,336,263 | 8/1994 | Ersek et al. . |
| 5,352,182 | 10/1994 | Kalb et al. . |

FOREIGN PATENT DOCUMENTS

| | | |
|---|---|---|
| 2023531 | 2/1992 | Canada . |
| 2941060 | 4/1980 | Germany .................................. 606/6 |
| 3247793 | 7/1983 | Germany .................................. 606/6 |
| 2121675 | 5/1990 | Japan ..................................... 604/22 |
| 9116859 | 11/1991 | WIPO ..................................... 604/22 |
| 9210142 | 6/1992 | WIPO ..................................... 604/22 |
| WO94/21307 | 9/1994 | WIPO . |
| WO94/21324 | 9/1994 | WIPO . |

OTHER PUBLICATIONS

Kabalin, John N.; Treatment of Post–Prostatectomy Stress Urinary Incontinence with Periurethral Polytetrafluoroethylene Past Injection. The Journal of Urology, vol. 152, 1463–1466, Nov. 1994; pp. 1464–1466.

Kageyama, Shinji et al; Collagen Implantation for Post--Prostatectomy Incontinence: Early Experience with a Transrectal Ultrasonographically Guided Method; The Journal of Urology, vol. 152, 1473–1475, Nov. 1994; pp. 1473–1475.

McQuire, Edward J. et al; Transurethral Collagen Injection for Urinary Incontinence; Urology, Apr. 1994, vol. 43, No. 4; pp. 413–415.

*Primary Examiner*—Manuel Mendez
*Attorney, Agent, or Firm*—Flehr, Hohbach, Test, Albritton & Herbert

[57] ABSTRACT

A medical device which includes an elongate probe member sized to be able to enter a urethra of a female human body and having a length so that when the distal extremity is disposed in the vicinity of a target volume of tissue surrounding the urethra the proximal extremity is outside of the urethra. The elongate probe member has a passage extending from the proximal extremity to the distal extremity. At least one tubular needle is disposed in the passage and has first and second extremities and a flow passageway therein extending longitudinally from the first extremity to at least one opening provided in the second extremity of the at least one tubular needle. A control handle is secured to the proximal extremity of the elongate probe member for causing movement of the at least one tubular needle in the passage. A guide passageway causes movement of the at least one tubular needle through a curved path extending at an angle to the longitudinal axis. A supply assembly is carried by the proximal extremity of the elongate probe member and is in communication with the flow passageway of the at least one tubular needle for introducing an agent into the flow passageway. A method for use of the device is provided.

17 Claims, 4 Drawing Sheets

FIG_1

FIG_4

FIG_3

FIG_5

FIG_2

FIG_10

FIG_7

FIG_9

FIG_6

TRANSURETHRAL NEEDLE DELIVERY DEVICE WITH CYSTOSCOPE AND METHOD FOR TREATMENT OF URINARY INCONTINENCE

This invention pertains generally to transurethral medical devices for treating urinary incontinence in humans and, more particularly, to transurethral medical devices with needles for penetrating the urethra of human females.

A large number of humans suffer from urinary incontinence, including a significant number of elderly females and nursing home residents. Stress urinary incontinence, which refers to the sudden leakage of urine with coughing, sneezing, exercise or activities that increase intra-abdominal pressure, most commonly occurs in women following childbearing or in men following prostatic surgery. Procedures have heretofore been provided for treating urinary incontinence. However, none of these modalities have proven to be optimal in all cases. There is, therefore, a need for a device and method for treating urinary incontinence which overcomes these disadvantages.

In general, it is an object of the present invention to provide a device and method for the treatment of urinary incontinence.

Another object of the invention is to provide a device and method of the above character in which an agent is introduced into tissue surrounding the urethra to add support to the sphincter muscle.

Another object of the invention is to provide a device and method of the above character in which the agent is introduced into a void in the tissue.

Another object of the invention is to provide a device and method of the above character in which the agent is introduced into a void created in the tissue by radio frequency ablation.

Another object of the invention is to provide a device and method of the above character in which the agent is heated during introduction into the tissue to prevent solidification of the agent prior to introduction.

Another object of the invention is to provide a device and method of the above character in which the agent is heated after its introduction into the target volume of tissue to facilitate solidification of the agent therein.

Another object of the invention is to provide a device and method of the above character in which the agent is heated after its introduction into the target volume by applying radio frequency energy thereto.

Another object of the invention is to provide a device and method of the above character in which the agent is simultaneously introduced into a plurality of target volumes within tissue surrounding the urethra.

Additional objects and features of the invention will appear from the following description from which the preferred embodiments are set forth in detail in conjunction with the accompanying drawings.

In general, a medical device is provided for use in a female human body to deliver an agent to a target volume of tissue surrounding a urethra in the body. The tissue includes a sphincter muscle and the urethra is formed by a urethral wall extending from a bladder to the exterior of the body. The device includes an elongate probe member having proximal and distal extremities and a longitudinal axis. The elongate probe member is sized to be able to enter the urethra and has a length so that when the distal extremity is disposed in the vicinity of the target volume of tissue the proximal extremity is outside of the urethra. The elongate probe member has a passage extending from the proximal extremity to the distal extremity. At least one tubular needle is disposed in the passage and has first and second extremities and a flow passageway therein extending longitudinally from the first extremity to at least one opening provided in the second extremity of the at least one tubular needle. A control handle is secured to the proximal extremity of the elongate probe member. Operative means is carried by the control handle and is connected to the first extremity of the at least one tubular needle for causing movement of the at least one tubular needle in the passage. Means is carried by the elongate probe member for causing movement of the at least one tubular needle through a curved path extending at an angle to the longitudinal axis. Means is carried by the proximal extremity of the elongate probe member and in communication with the flow passageway of the at least one tubular needle for introducing the agent into the flow passageway. When the at least one tubular needle is advanced through the urethral wall under the control of the operative means at least the opening in the second extremity of the tubular needle has been advanced into the target volume to permit the agent to be introduced through the flow passageway and opening in the tubular needle into the target volume so as to add support to the sphincter muscle.

A method is provided to deliver an agent to a target volume of tissue surrounding a urethra in a human body. The tissue includes a sphincter muscle and the urethra is formed by a urethral wall extending from a bladder to the exterior of the body. The method includes the step of advancing a tubular needle having a free extremity with at least one opening therein into tissue surrounding the urethra wall so that the opening is in the target volume. The agent is introduced into the target volume so as to add support to the sphincter muscle.

More in particular, transurethral needle delivery medical device 20 of the present invention is for use in treating urinary incontinence, specifically stress urinary incontinence in females. In this regard, device 20 can be utilized to inject a suitable agent or medication such as a compound 21 into the tissue surrounding the urethra immediately above and below the sphincter urethrae muscle. Delivery device 20 illustrated in FIGS. 1–5 includes an up to 26 French catheterlike elongate tubular probe member or probe 22 having a length ranging from four to twelve centimeters. Body or probe 22 is provided with proximal and distal extremities 22a and 22b and, as particularly shown in FIGS. 2 and 3, is formed with a sidewall 26 which is generally circular in cross section. A longitudinal axis 27 extends between proximal and distal extremities 22a and 22b and sidewall 26 serves to form a passage 31 extending longitudinally through probe 22. Passage 31 is closed at distal extremity 22b by blunt end 33. At least one and as illustrated in FIG. 1 a plurality of four circumferentially spaced-apart openings 36 extend through sidewall 26 at distal extremity 22b of probe 22.

Figure 1:
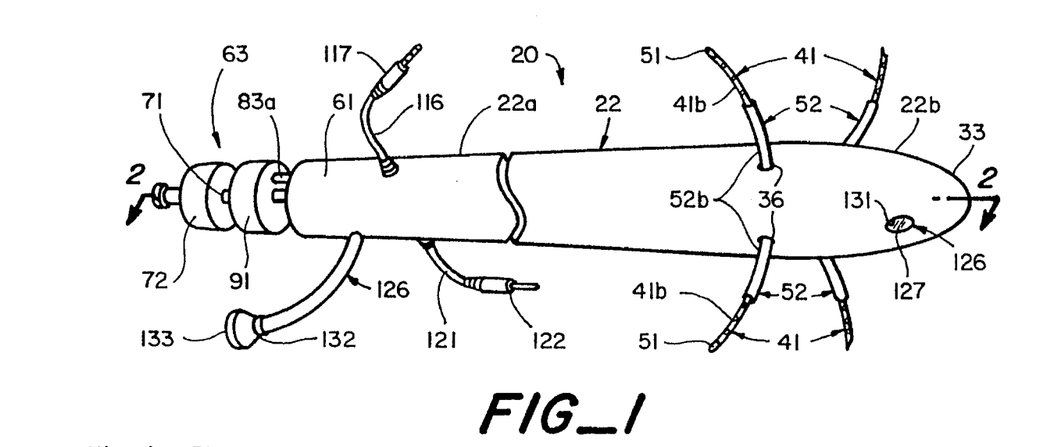
FIG. 1 is a perspective view of an embodiment of the transurethral needle delivery device of the present invention.
Figure 2:
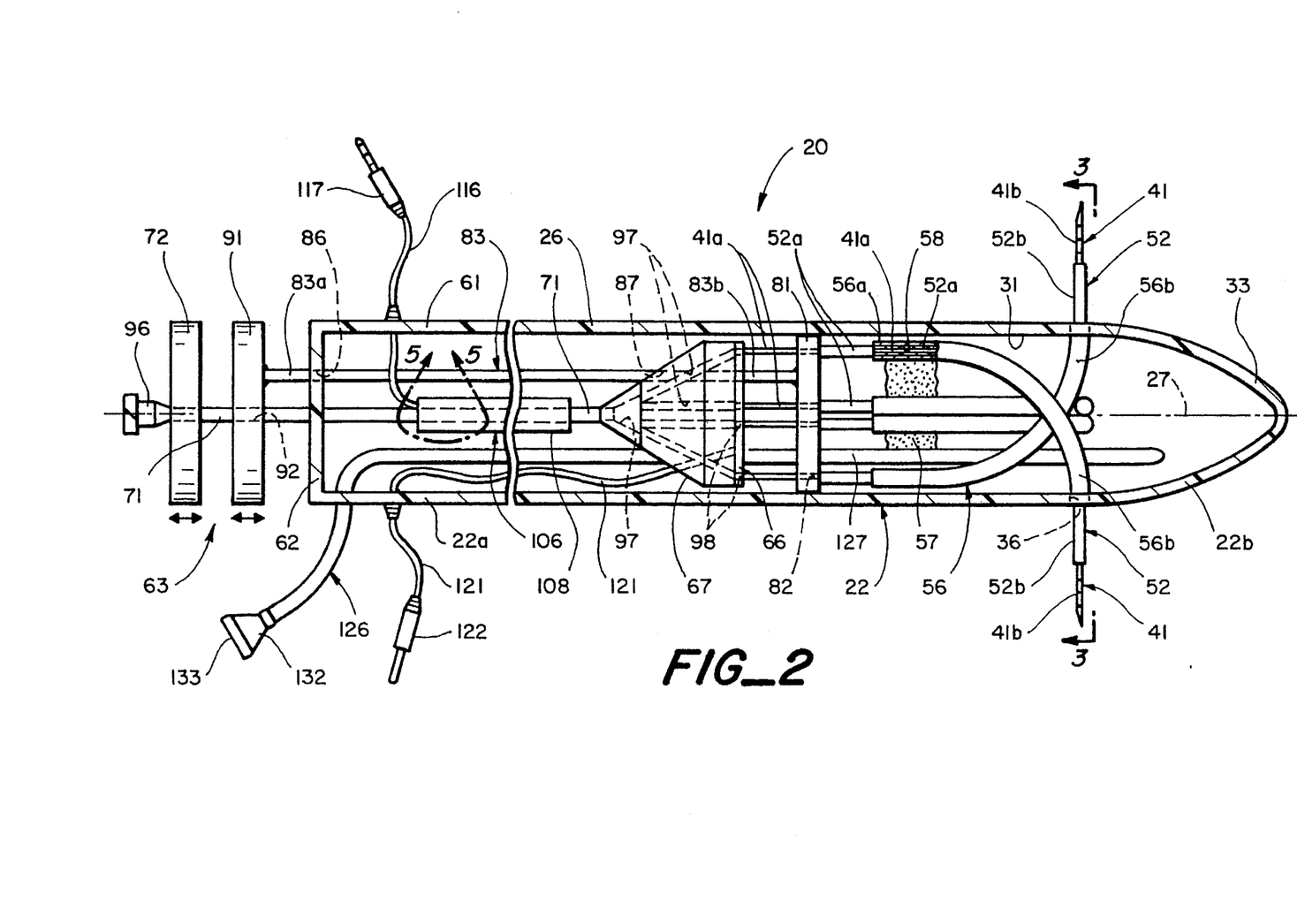
FIG. 2 is a cross-sectional view of the transurethral needle delivery device of FIG. 1 taken along the line 2—2 of FIG. 1.
Figure 3:
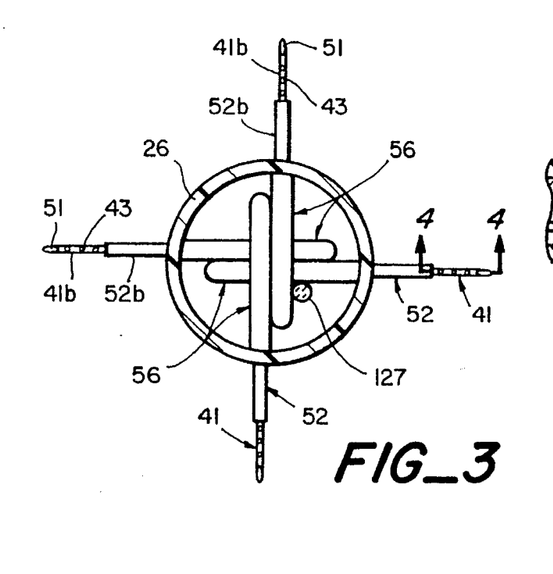
FIG. 3 is a cross-sectional view of the transurethral needle delivery device of FIG. 1 taken along the line 3—3 of FIG. 2.
Figures 4, 5:
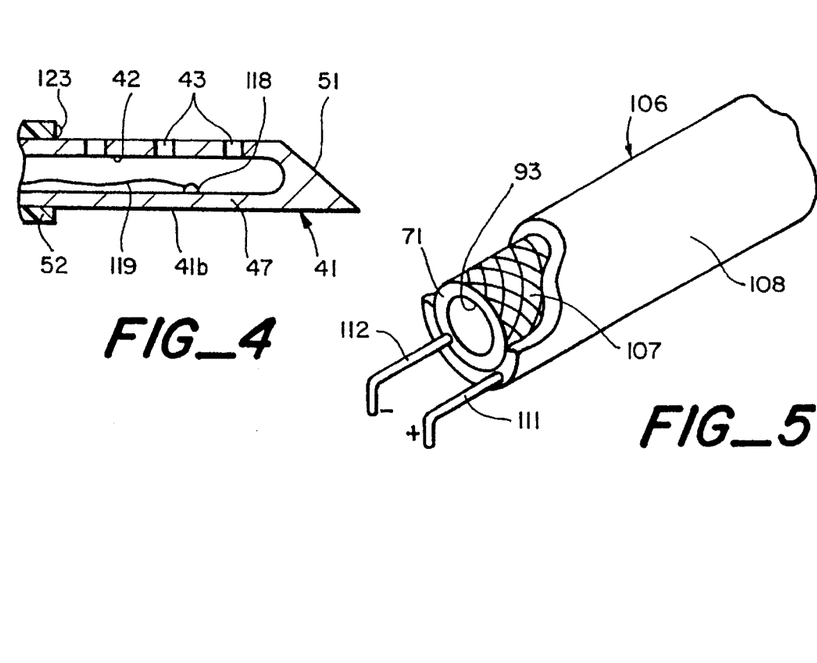
FIG. 4 is a cross-sectional view of the transurethral needle delivery device of FIG. 1 taken along the line 4—4 of FIG. 3.
FIG. 5 is an enlarged isometric view, partially cut away, of the transurethral needle delivery device of FIG. 1 taken along the line 5—5 of FIG. 2.

At least one and as shown in FIGS. 1–3 a plurality of four tubular radio frequency needles or electrodes 41 are carried by probe 22 for slidable disposition from the probe in generally planar directions which are generally perpendicular to longitudinal axis 27. Electrodes 41 are made from an electrically conductive material such as stainless steel and are formed with a flow passageway 42, identified in FIG. 4, which extends longitudinally between first or proximal and second or distal extremities 41a and 41b thereof. Electrodes 41 are generally circular in cross section and have an internal cross-sectional area dependent upon, among other things, the viscosity of compound 21. More specifically, electrodes 41 each have an outer diameter ranging from 0.3 to 1.2 millimeter and an inner diameter ranging from 0.2 to 1.0 millimeter and preferably approximately 0.5 millimeter. Each of electrodes 41 is formed with at least one and as illustrated in the drawings a plurality of openings or side ports 43 longitudinally spaced-apart over a portion of distal extremity 41b. Ports 43 extend through sidewall 47 of each electrode so as to be in communication with flow passageway 42 therein. As shown in FIG. 4, each of electrodes 41 is provided with a closed sharpened tip 51.

A sheath or sleeve 52 made from any suitable insulating material such as plastic is coaxially disposed on each of electrodes 41 for longitudinal slidable movement relative to the electrode. Insulating sleeves 52 have a suitable wall thickness, such as approximately 0.05 millimeter, and have first or proximal and second or distal extremities 52a and 52b.

Probe 22 is provided with guide means in the form of guide tubes 56 for guiding electrodes 41 and insulating sleeves 52 in a curved path within passage 31 so that free or distal extremities 41b and 52b extend outwardly from sidewall 26 of the probe in the desired directions. Guide tubes or cannulas 56 are made from any suitable material such as stainless steel and have first or proximal and second or distal end portions 56a and 56b. The guide cannulas each extend within probe 22 through a curve of approximately 90° between their respective end portions. Proximal end portions 56a extend generally longitudinally within the probe, being potted or otherwise secured therein by any suitable means such as an adhesive 57, and distal end portions 56b are cooperatively coupled or secured within an opening 36 in sidewall 26 by any suitable means such as an adhesive (not shown) so as to be generally flush with the exterior of sidewall 26 (see FIGS. 2 and 3). The guide tubes 56 are each provided with a guide passageway or lumen 58 extending longitudinally therethrough from proximal end portion 56a to distal end portion 56b for slidably receiving therein an insulating sleeve 52 having an electrode 41 slidably disposed therein. In this manner, guide tubes 56 are included within the means of device 20 for causing movement of electrodes 41 through a curved path extending at an angle to longitudinal axis 27. Alternatively, the guide means of the present invention could be in the form of a single molded element (not shown) secured within or formed integral with probe 22 and having lumens similar to lumens 58 formed therein.

A control handle 61 is secured to proximal extremity 22a of probe 22. More specifically, control handle 61 is formed integral with probe 22 and includes an end wall 62.

Operative means 63 is carried by the control handle 61 for causing movement of electrodes 41 and insulating sleeves 52 in lumens 58 and includes a disc-like bus 66 made from any suitable material such as brass disposed transverse to longitudinal axis 27 within passage 31 and soldered or otherwise suitably joined to opposite or proximal extremities 41a of electrodes 41. A generally conical manifold 67 made from any suitable material such as plastic or steel is secured by an adhesive or any other suitable means (not shown) to the proximal side of bus 66. An elongate tube 71 made from stainless steel or any other suitable conductive material is press fit into or otherwise suitably joined to the center of the narrowed proximal end of manifold 67 and extends along longitudinal axis 27 through an opening in the center of end wall 62. Tube 71 is press fit into or otherwise suitably joined at its proximal end to a first or needle deploy knob 72 which is made from any suitable material such as plastic and is longitudinally movable in the directions shown in FIG. 2.

Operative means 63 further includes a disc-like bushing or piston 81 transversely disposed within passage 31 between guide tubes 56 and manifold 67. Piston 81 is made from plastic or any other suitable material and is provided with a plurality of four bores 82 extending longitudinally therethrough which are aligned so as to permit the passage of proximal extremities 41a of electrodes 41 therethrough. Proximal extremities 52a of insulating sleeves 52 are press fit into bores 82 or otherwise secured to piston 81. A push/pull rod 83 made from stainless steel or any other suitable material and having proximal and distal end portions 83a and 83b extends through a hole 86 in end wall 62 and a bore 87 in manifold 67. Distal end portion 83b of the push/pull rod is press fit into or otherwise suitably secured to piston 82 and proximal end portion 83a is likewise secured to a second or insulation knob 91 made from plastic or any other suitable material and disposed between end wall 62 and needle knob 72. Insulation knob 91 is provided with a bore 92 extending through its center so as to be axially slidable in the directions shown in FIG. 2 along tube 71 extending through the bore 92.

Means in the form of a supply assembly is carried by proximal extremity 22a of probe 22 for introducing compound 21 into flow passageways 42 of electrodes 41 and includes a fitting 96 secured to the proximal end of tube 71. Tube 71 is provided with a central lumen 93, identified in FIG. 5, for carrying compound 21 to dispersal passageways 97 provided within manifold 67 and illustrated in FIG. 2. Dispersal passageways 97 are in communication with a plurality of bores 98 provided in bus 66 and aligned with flow passageways 42 in electrodes 41.

An in-line heater 106 is coaxially carried by tube 71 and is included within the means of device 20 for heating compound 21 as it travels through tube 71. Heater 106 includes a resistive coating 107 made from any suitable material such as iron oxide circumferentially disposed around a portion of tube 71 and a sleeve or jacket 108 made from stainless steel or any other suitable conductive material disposed around coating 107. Jacket 108 can be covered with a thermally or electrically insulative coating (not shown) to preclude undesirable current and heat transfer into the tissue. Electrical leads 111 and 112 are respectively connected to tube 71 and tubular jacket 108 and are carried within a wire 116 which extends through sidewall 26 and is provided with a connector 117 at the end thereof for providing electrical energy to heater 106. Device 20 is provided with a first temperature sensing means in the form of at least one first thermocouple 118 mounted within a flow passageway 42 of an electrode 41 for monitoring the temperature of compound 21 as it flows from side ports 43 (See FIG. 4). A lead 119, a portion of which is illustrated in FIG. 4, extends therefrom to proximal extremity 22a of probe 22.

Alternatively, the means for heating compound 21 could be in the form of an electrical wire (not shown) extending longitudinally down and secured within central lumen 93 of tube 71. This wire would serve to supply heat to the compound flowing within lumen 93 when electrical energy is supplied to the wire.

Radio frequency, microwave or other electrical energy can be supplied to electrodes 41 through an additional lead or wire 121 which extends through sidewall 26 and manifold 67 for electrical connection to bus 66. Wire 121 is provided with a plug 122 at the end thereof for connecting to an appropriate generator or energy source (not shown). Device 20 is provided with a second temperature sensing means in the form of at least one second thermocouple 123 mounted at the tip of an insulating sleeve 52 for monitoring the temperature in the body tissue in the area of electrode 41. A lead (not shown) extends therefrom to proximal extremity 22a of probe 22.

Device 20 further includes a cystoscope 126 formed with a fiber or rod optical element 127 extending longitudinally through manifold 67, bus 66 and piston 81 in passage 31. Blunt end 33 of probe 22 is formed with an opening 131 therein into which the distal end of optical element 127 extends. Cystoscope 126 has a fitting 132 at the proximal end of optical element 127 and an eye piece 133 is carried by the fitting 132.

Although device 20 illustrated in the drawings is provided with an insulating sheath or sleeve 52 for moving longitudinally along each of electrodes 41, an alternate embodiment of device 20 can be provided for procedures hereinafter described in which each of sleeves 52 is fixedly secured to the respective electrode 41 and does not slide thereon. In this embodiment of the device of the invention, not illustrated in the drawings, piston 81 could be mounted to the inside of probe 22 by any suitable means such as an adhesive and push/pull rod 83 and insulation knob 91 eliminated.

Operation and use of transurethral needle delivery device 20 in conjunction with performing a procedure on a human female patient suffering from stress urinary incontinence may now be briefly described as follows. The female patient 141 to undergo the procedure is partially shown in FIG. 6 in which the anatomy of interest is disclosed and as shown consists of a bladder 142 which is provided with a base or bladder neck 143 which empties into a urethra 146 formed by an endothelial lining or urethral wall 147 extending to the external meatus 148 or exterior of the body. Tissue 151 surrounding urethral wall 147 includes adipose tissue 152, sphincter urethrae muscle 153 and adipose tissue 156.

Assuming that the patient's pretreatment evaluation warrants the use of the transurethral procedure hereinafter described, patient 141 can be brought into an out patient clinic or an operating room in a hospital. The patient is prepped and draped in the dorsal lithotomy position. If radio frequency or other electrical energy is to be applied through electrodes 41, a conventional indifferent or grounding electrode (not shown) may be placed on the patient's backside so that it is adherent thereto and makes good electrical contact with the skin of the patient. Connector 117 of wire 116 and plug 122 of wire 121 are connected into a control console electrical source and a radio frequency or other appropriate generator (not shown). Device 20 is prepared by pulling knobs 72 and 91 rearwardly so that electrodes 41 and insulating sleeves 52 thereon are fully retracted within guide tubes 56.

Figure 6:
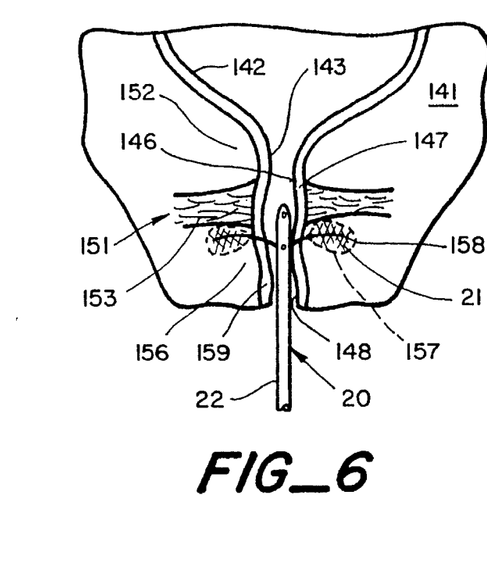
FIG. 6 is an illustration of a portion of the transurethral needle delivery device of FIG. 1 in place within the urethra of a female human body.
Figure 7:
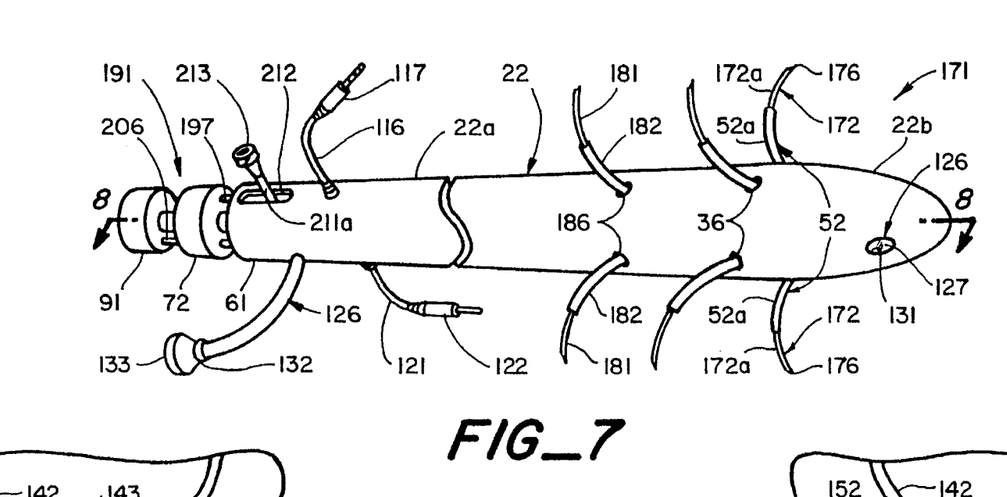
FIG. 7 a perspective view of another embodiment of the transurethral needle delivery device of the present invention.
Figure 8:
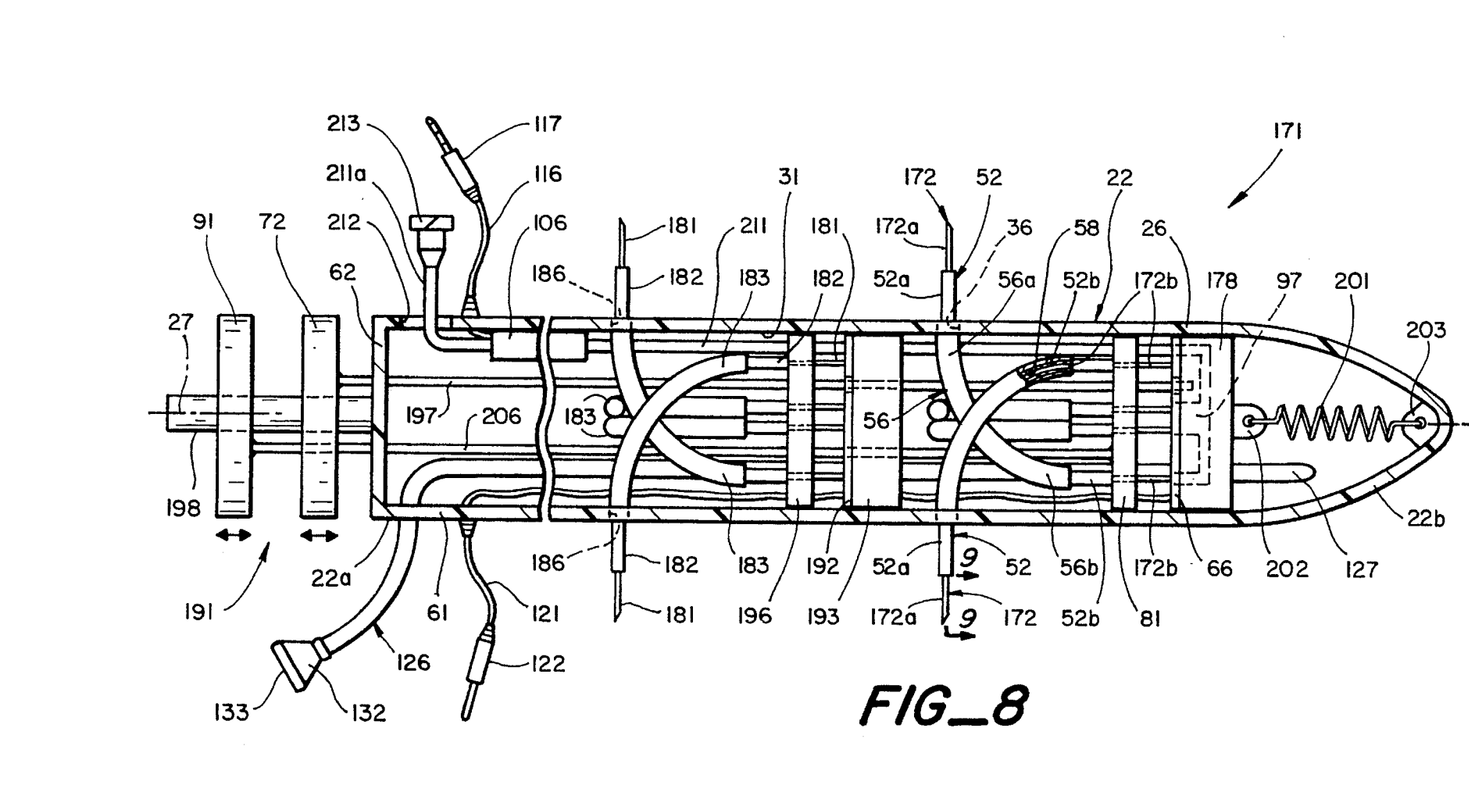
FIG. 8 is a cross-sectional view of the transurethral needle delivery device of FIG. 7 taken along the line 8—8 of FIG. 7.
Figure 9:
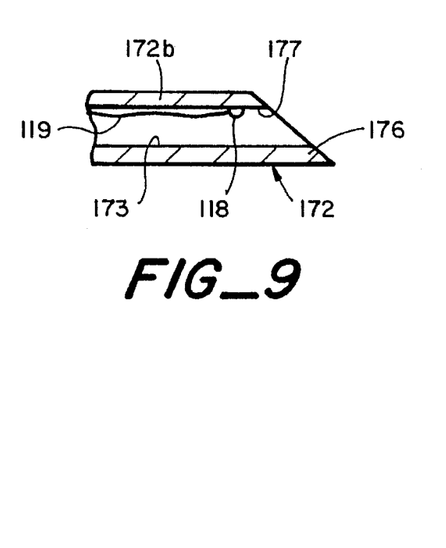
FIG. 9 is a cross-sectional view of the transurethral needle delivery device of FIG. 7 taken along the line 9—9 of FIG. 8.

The physician then introduces a lubricating jelly with a local anesthetic such as Lidocaine into urethra 146 utilizing a syringe (not shown) to make it possible for the urethra to accommodate probe 22. After this has been accomplished, the physician introduces distal extremity 22b of probe 22 into urethra 146 and progressively advances the probe while viewing its position through eye piece 133 of cystoscope 126. Utilizing the anatomy of the female urethra visible through cystoscope 126, the physician is able to properly identify the location within the urethra where he/she wishes to deliver the therapy. In FIG. 6, for example, probe openings 36 are located in the vicinity of target volumes 157 within adipose tissue 156. As can be seen, probe 22 is diametrically sized so as to be able to enter urethra 146 and has a length so that when distal extremity 22b thereof is in the vicinity of the target volume 157 of tissue 151, proximal extremity 22a of the probe is outside of urethra 146.

Once distal extremity 22b of probe 22 has been desirably positioned within urethra 146, for example as shown in FIG. 6, needle knob 72 and insulation knob 91 are pushed forwardly relative to control handle 61 so as to advance fenestrated electrodes 41 and insulating sleeves 52 out of guide tubes 56 and openings 36 in sidewall 26. The pushing of knobs 72 and 91 causes electrodes 41 to extend generally radially from longitudinal axis 27 and penetrate urethral wall 147, closely followed by insulating sleeves 52. Knobs 72 and 91 are thereafter longitudinally adjusted relative to control handle 61 until electrode tips 51 have been advanced a preselected length from sidewall 26 so that at least the portions of electrode distal extremities 41b having side ports 43 therein have been advanced beyond the end of insulating sleeves 52. Where sleeves 52 and electrodes 41 are capable of relative longitudinal movement, it is desirable that distal extremities 52b of insulating sleeves 52 be advanced and then retracted relative to electrodes 41 so as to minimize any tenting of urethral wall 147.

The proximal end of tube 71 and proximal end portion 83a of rod 83 can be provided with appropriate markings (not shown) so that their respective positions relative to end wall 62 of control handle 61 indicates the respective positions of electrodes 41 and insulating sleeves 52 relative to sidewall 26. It should be appreciated that electrodes 41 can be moved inwardly and outwardly relative to insulating sleeves 52 and that the insulating sleeves can be moved relatively inwardly and outwardly relative to sidewall 26 in so positioning electrodes 41 and insulating sleeves 52 within target volumes 157 of tissue 151.

When electrodes 41 and insulating sleeves 52 have been so deployed within tissue 151, distal extremities 41b and 52b thereof extend generally radially outwardly from probe 22 in a planar array. The electrodes and insulating sleeves are circumferentially spaced-apart about longitudinal axis 27 at angles of approximately 90°.

Radio frequency energy can then be provided through wire 121 to electrodes 41 so that tissue 151 surrounding the electrode distal extremities 41b is ablated to create voids in the tissue 151. Radio frequency energy is supplied from the control console and a radio frequency generator (not shown). Typically, the radio frequencies can range from 300 kHz to 26 mHz. The radio frequency energy is delivered at power levels which range from 2 to 80 watts. The time of application of radio frequency energy can range from five seconds to five minutes and in certain procedures could vary over time. The size of voids 158 is dependent upon, among other things, the number of agent placement cites and the amount of narrowing required within the urethra. During this ablation procedure, insulating sleeves 52, which have been advanced through urethral wall 147, protect the urethral wall from radio frequency ablation. Second thermocouple or thermocouples 123 permit monitoring of the power output of electrodes 41 by measuring the temperature of tissue 151 adjacent to the ablating electrodes.

After the creation of voids 158 as hereinbefore described, a suitable anesthetic such as Lidocaine can be introduced through electrodes 41 into the voids if desired to numb the local tissue and thereby make the patient more comfortable. Thereafter, a suitable compound or biocompatible resin, for example, a side-chain crystallizable (SCC) polymer such as "Intelimer" SCC polymers made by Landec Corporation of Menlo Park, Calif., is introduced into voids 158 via fitting 96, tube 71, dispersal passageways 97, bores 98 and flow passageways 42 and side ports 43 of electrodes 41. The plurality of side ports 43 on electrode needles 41 facilitate the even distribution of compound 21 within voids 158. As appreciated by those skilled in the art, compounds such as SCC polymers can be delivered in an amorphous or viscous state at a temperature higher than that of normal body temperature and thereafter crystallizes upon being cooled to body temperature. Heater 106 of device 20 permits delivery of such SCC polymers by maintaining the polymers at the desired temperature above body temperature while they are introduced through probe 22. First thermocouple or thermocouples 118 permit monitoring of the temperature of the polymer prior to its introduction into tissue 151 to ensure that the polymer is maintained at a temperature above its melt point. Once the SCC polymer reaches a void 158, it crystallizes or solidifies as its temperature decreases to body temperature.

When a compound 21 such as a hereinabove described SCC polymer is so placed within voids 158 and tissue 156, it serves to support sphincter muscle 153 in the localized zone where the compound has been injected. The compound provides concentric mechanical pressure on urethral wall 147 and increases the closure forces exerted by the sphincter muscle upon urethra 146. In this manner, the diameter of the urethra extending through the sphincter muscle 153 is reduced so as to narrow or close the urethra and thus decrease involuntary loss of urine through the urethra. The circumferential injection of compound 21 around urethra 146 leaves the urethra and adjacent tissue sufficiently pliable to accomplish closure when in a relaxed state, yet pliable enough to allow passage of urine and bladder contraction. The injection of compound 21 into voids 158 hinders undesirable migration of the compound within the tissue of surrounding urethra 146.

After compound 21 has been so injected into tissue 156, knobs 72 and 91 are retracted relative to control handle 61 so that electrodes 41 and insulating sleeves 52 are fully retracted into guide tubes 56. Thereafter, if deemed necessary by the physician, device 20 can be rotated approximately 45° within urethra and electrodes 41 and insulating sleeves 52 similarly redeployed for creating additional voids 158 within tissue 156 and the injection of additional compound 21. It is presently contemplated that compound 21 could be injected into target volumes ranging in number from four to twelve in any given procedure. It should also be appreciated that distal extremity 22b of probe 22 can be advanced further into urethra 146 for introducing or injecting compound 21 into adipose tissue 152 or even sphincter muscle 153 in the manner discussed above if so desired by the physician.

Once compound 21 has been delivered to the desired target volumes 157 within tissue 151 and electrodes 41 and insulating sleeves 52 have been fully retracted into guide tubes 56, probe 22 is removed from urethra 146. With the procedure completed, the patient can rest for a short period of time and then leave the procedure room and go to her home.

Although the method hereinbefore described has included the creation of voids 158 through the application of radio frequency energy to tissue 151 via electrodes 41, it should be appreciated that compound 21 can be injected into target volumes 157 of tissue 151 without first creating voids therein and be within the scope of the present invention. In a procedure of this type, compound 21 is injected directly into tissue 151 having no voids 158 formed therein. If radio frequency energy to electrode 41 is not required for heating the agent after its introduction into tissue 151, the device of the present invention for this procedure could have a dielectric coating or insulative nonslidable sleeve 52 carried about each of electrodes 41.

Device 20 of the present invention can also be utilized for delivering a compound 21 such as a cross-linkable collagen which is in an amorphous or viscous state at body temperature and cross-links and solidifies after being exposed to heat. In this regard, such a compound 21 can be introduced into tissue such as the submucosal tissues 159 immediately beyond urethra wall 147 by device 20 without the use of heater 106. Although the injected collagen can be left in submucosal tissue 159 without further treatment by device 20, radio frequency, microwave or other electrical energy can thereafter be supplied to electrodes 41 to heat the collagen and cause it to polymerize and solidify. Such solidification hinders migration of the collagen and increases its support of sphincter muscles 153. Second thermocouple or thermocouples 123 permit monitoring of the temperature of tissue 151 to, among other things, ensure that urethral wall 147 is not burned. The collagen acts upon sphincter muscle 153 in the same manner as discussed above to decrease involuntary urine loss. It should be appreciated that compound 21 can be heated for curing by other methods, such as induction, ultrasound, resistive heating, chemically through the reaction of appropriate chemicals or electromagnetic energy, and be within the scope of the present invention. Such a procedure could be accomplished without the creation of voids 158.

It should be appreciated that the methods of the invention hereinabove described can be combined or altered in a single procedure and be within the scope of the present invention. For example, device 20 can be utilized for injecting a SCC polymer, with or without the prior creation of voids 158, and then utilized for injecting a collagen into the submucosal tissue.

An additional embodiment of the transurethral needle delivery device of the present invention is illustrated in FIGS. 7–10. Device 171 shown therein is substantially similar to device 20 and like reference numbers have been used to identify like elements or components of device 171. Device 171 includes at least one tubular needle or electrode. More specifically, as shown in the drawings, device 171 has a first set of tubular needles or electrodes 172 which are substantially similar to electrodes 41 of device 20 and have opposite second or proximal and first or distal extremities 172a and 172b. First electrodes 172 each have a flow passageway 173, illustrated in part in FIG. 9, extending between distal and proximal extremities 172a and 172b. Each electrode 172 has at least one opening in free or proximal extremity 172a thereof and has an open sharpened tip 176 into which flow passageway 173 extends at opening 177.

Electrodes 172 and the insulating sleeves 52 coaxially mounted thereon are slidable relative to each other and are slidably carried within guide tubes 56. Opposite or distal extremities 172b of the first electrodes are secured to bus 66 mounted on a manifold 178 substantially similar to manifold 67 and first or distal extremities 52b of insulating sleeves 52 are mounted to piston 81. Manifold 178 and piston 81 permit slidable disposition of electrodes 172 and insulating sleeves 52 from openings 36 and probe distal extremity 22b so that the electrodes and insulating sleeves generally extend from the probe in a plane with the electrodes and respective sleeves spaced apart approximately 90° in that plane.

Device 171 includes an additional or second set of four tubular needles or electrodes 181 which are substantially identical to first electrodes 172 and are carried by probe 22 proximal of first electrodes 172. A second insulating sleeve 182 substantially identical to insulating sleeve 52 is coaxially and slidably carried by each second electrode 181 and the second electrodes and insulating sleeves are slidably carried within second guide tubes 183. An additional or second set of four openings 186 are provided in probe 22. Openings 186 are circumferentially spaced apart about longitudinal axis 27 at approximately 90° intervals and each of second guide tubes 183 has a proximal extremity secured within a respective opening 186.

Device 171 includes operative means 191 substantially similar to operative means 63 of device 20. Operative means 191 simultaneously deploys or retracts each of electrodes 172 and 181 and simultaneously deploys or retracts each of insulating sleeves 52 and 182. Like operative means 63, the operative means of device 171 permits relative movement between the electrodes and related insulating sleeves of the device.

Operative means 191 includes needle and insulation knobs 72 and knob 91 and bus 66, manifold 178 and piston 81 discussed above. The operative means 191 further includes a second bus 192 and manifold 193, substantially similar to bus 66 and manifold 67, onto which second electrodes 181 are mounted for actuation. Second insulating sleeves 182 are mounted to a second piston 196 which is substantially similar to piston 81 onto which insulating sleeves 52 of device 171 are mounted. A first pull/push rod 197 made from any suitable material such as stainless steel extends longitudinally through pistons 81 and 196 and buses 66 and 192 in probe 22. Rod 197 is secured to each of manifolds 178 and 193 and to needle knob 72 for moving electrodes 172 and 181 within respective guide tubes 56 and 183. Knob 72 is concentrically, slidably carried by a stem 198 secured to the center of end wall 62 and extending proximally thereof along longitudinal axis 27 and knob 72 is provided with a central bore through which stem 198 extends. First and second needle electrodes 172 and 181 of device 171 are urged toward their respective distal or retracted positions by a return spring 201 extending longitudinally within distal extremity 22b of probe 22. Spring 201 has a proximal end secured to a tab 202 formed on manifold 178 and a distal end secured to an eyelet 203 formed inside the tip of blunt end 33 of probe 22.

A second pull/push rod 201 made from stainless steel or any other suitable material extends longitudinally through second bus and manifold 192 and 193 slidably carried within the probe 22 of device 171 and is secured by any suitable means such as an adhesive to pistons 196 and 81 of the device. The proximal end of rod 201 slidably extends through end wall 62 of control handle 61 and needle knob 72 and is secured to insulation knob 91 so as to permit deployment and retraction of the insulating sleeves of device 171. Knob 91 slidably rides on central stem 198 and is provided with a central bore through which stem 198 extends.

Device 171 includes means carried by proximal extremity 22a of probe 22 for introducing compound 21 into the flow passageways of electrodes 172 and 181. This means or supply assembly includes a tube 211 extending longitudinally through device 171 and having a central lumen (not shown) in communication with dispersal passageways 196 within manifold 178 and similar dispersal passageways (not shown) provided within second manifold 193. Tube 211 includes a proximal end portion 211a which extends through a longitudinally extending slot 212 in sidewall 26 and is provided with a fitting 213 on the end thereof. Slot 212 permits proximal end portion 211a of tube 211 to move proximally and distally with manifolds 178 and 193 relative to probe 22.

Device 171 operates in substantially the same manner as device 20 described above except that, unlike the operative means of device 20, the operative means 191 of device 171 causes deployment of electrodes 172 and 181 and/or insulating sleeves 52 and 182 when the physician pulls on respective knobs 72 and/or 91 rather than pushing on the knobs. Conversely, the electrodes and insulating sleeves are retracted by pushing knobs 72 and 91 of device 171 toward control handle 61.

Figure 10:
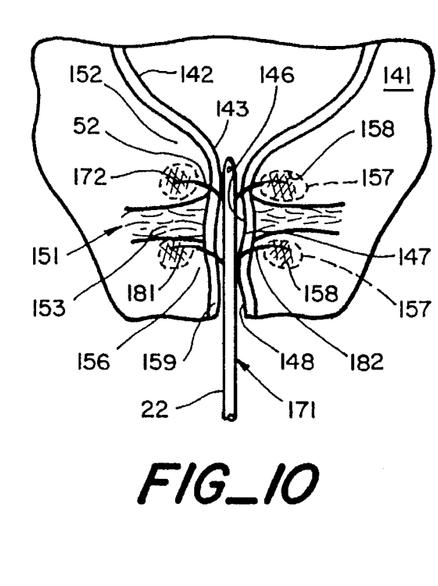
FIG. 10 is an illustration of a portion of the transurethral needle delivery device of FIG. 7 in place within the urethra of a female human body.

Additional electrodes 181 of device 171 permit a greater amount of compound 21 to be simultaneously introduced into tissue 151 than possible with device 20 described above. The increased deployment efficiency of device 171 decreases the length of the procedure to the advantage of patient 141. The pull-deployment arrangement of device 171 facilitates the inclusion of second electrodes 181. As illustrated in FIG. 10, device 171 is particularly suited for the simultaneous introduction or injection of compound 21 into adipose tissue 152 and 156.

It should be appreciated that the transurethral needle delivery device herein provided can have other configurations and be within the scope of the present invention. A probe could be provided similar to probe 22 but having only a single tubular needle or electrode 41 and corresponding insulating sleeve 52 at its distal extremity. In operation of such a device, the single electrode and insulating sleeve could be repeatedly advanced into tissue 151 for the introduction of the agent therein as the device is sequentially rotated about its longitudinal axis in the desired portion of urethra 146. Alternatively, a device having a plurality of electrodes lesser or greater than four in each planar electrode array would also be within the scope of the present invention.

Although the transurethral needle delivery device and method of the present invention have been described as treating urinary incontinence in females, it should be appreciated that utilization of the device and/or method for the treatment of urinary incontinence in males would be within the scope of the present invention. It should also be appreciated that devices 20 or 171 can be utilized for performing radio frequency ablations within tissue 151 in a procedure not involving the injection of compound 21 in the tissue and be within the scope of the present invention.

In view of the foregoing, it can be seen that a device and method for the treatment of urinary incontinence has been provided. The device and method provides for the introduction of an agent into tissue surrounding the urethra to add support to the sphincter muscle. The agent can be introduced into a void created in the tissue by radio frequency ablation and can be heated during introduction into the tissue to prevent solidification of the agent prior to introduction. The agent can be heated by the application of radio frequency or other energy thereto after its introduction into the target volume of tissue if necessary to facilitate solidification of the agent therein. The device and method permits the agent to be simultaneously introduced into a plurality of target volumes within tissue surrounding the urethra.

What is claimed is:

1. A medical device for use in a female human body to deliver an agent to a target volume of tissue including a sphincter muscle which surrounds a urethra in the body to treat urinary incontinence, the urethra formed by a urethral wall extending from a bladder to the exterior of the body, comprising an elongate probe member having proximal and distal extremities and a longitudinal axis, the elongate probe member being sized to be able to enter the urethra and having a length so that when the distal extremity is disposed in the vicinity of the target volume of tissue the proximal extremity is outside of the urethra, the elongate probe member having a passage extending from the proximal extremity to the distal extremity, at least one tubular needle disposed in the passage and having first and second extremities and a flow passageway therein extending longitudinally from the first extremity to at least one opening provided in the second extremity, a control handle secured to the proximal extremity of the elongate probe member, operative means carried by the control handle and connected to the first extremity of the at least one tubular needle for causing movement of the at least one tubular needle in the passage and means carried by the elongate probe member for directing the at least one tubular needle through a curved path extending at an angle to the longitudinal axis as the at least one tubular needle moves in the passage, the tubular needle and the operative means included within means for introducing the agent into the target volume so as to add mechanical support to the sphincter muscle and thus increase the closure forces exerted by the sphincter muscle upon the urethra.

2. A device as in claim 1 wherein the at least one tubular needle is an electrode of an electrically conductive material.

3. A device as in claim 2 together with an insulating sleeve coaxially mounted on the electrically conductive electrode, the operative means connected to the insulating sleeve for causing relative movement between the insulating sleeve and the electrically conductive electrode.

4. A device as in claim 1 wherein the directing means directs the at least one tubular needle radially from the elongate probe member.

5. A device as in claim 1 wherein the at least one tubular needle includes a plurality of side ports in communication with the flow passageway.

6. A device as in claim 1 wherein the at least one tubular needle includes a plurality of tubular needles having second extremities, the operative means connected to the plurality of tubular needles and the directing means causing the tubular needles to extend through a curved path at an angle to the longitudinal axis so as to lie in circumferentially spaced-apart positions in a plane perpendicular to the longitudinal axis.

7. A device as in claim 6 together with a second plurality of tubular needles having second extremities, the operative means connected to the second plurality of tubular needles and the directing means causing the second plurality of tubular needles to extend through a curved path at an angle to the longitudinal axis so as to lie in circumferentially spaced-apart positions in a second plane perpendicular to the longitudinal axis and longitudinally spaced apart from the first named plane.

8. A device as in claim 1 together with a second tubular needle, the operative means connected to the second tubular needle and the directing means causing the second tubular needle to extend through a curved path at an angle to the longitudinal axis and longitudinally spaced apart, from the curved path of the at least one tubular needle.

9. A medical device for use in a female human body to deliver a crystallizable agent to target volumes of tissue surrounding a urethra therein formed by a urethral wall extending from a bladder to the exterior of the body comprising an elongate probe member having proximal and distal extremities and a longitudinal axis, the elongate probe member being sized to be able to enter the urethra and having a length so that when the distal extremity is disposed in the vicinity of the target volumes of tissue the proximal extremity is outside of the urethra, the elongate probe member having a sidewall and a passage extending from the proximal extremity to the distal extremity and having a plurality of circumferentially spaced-apart openings at the distal extremity extending through the side wall, a plurality of guide cannulas disposed in the passage having first and second end portions, each of the guide cannulas having a lumen extending therethrough from the first end portion to the second end portion and communicating with an opening in the side wall, a tubular radio frequency electrode of an electrically conductive material disposed in each lumen and having a flow passageway extending longitudinally therethrough, each tubular radio frequency electrode having a port in communication with the flow passageway and having a sharpened tip, an insulating sleeve coaxially disposed on each of the tubular radio frequency electrodes, a control handle secured to the proximal extremity of the elongate probe member, operative means carried by the control handle and secured to the tubular radio frequency electrodes and the insulating sleeves for causing movement of the tubular radio frequency electrodes and the insulating sleeves in the lumens whereby when the insulating sleeves and the tubular radio frequency electrodes are advanced from the openings in the sidewall under the control of the operative means, the insulating sleeves and the tubular radio frequency electrodes are advanced through the urethral wall so that at least a portion of each tubular radio frequency electrode has been advanced into one of the target volumes and is exposed in the target volume so that when radio frequency energy is supplied to the tubular radio frequency electrodes tissue is ablated in the target volumes surrounding said portions to create a void while the insulating sleeves protect the urethral wall from radio frequency ablation, the operative means and the tubular radio frequency electrodes included within means for introducing the crystallizable agent through the ports into the void in the target volumes of tissue so as to increase the closure forces exertable upon the urethra.

10. A method to deliver an agent to a target volume of tissue surrounding a urethra in a female human body to treat urinary incontinence, the tissue including a sphincter muscle and the urethra formed by a urethral wall extending from a bladder to the exterior of the body, comprising advancing a tubular needle having a free extremity with at least one opening therein into tissue surrounding the urethra wall so that the opening is in the target volume and introducing the agent into the target volume to add mechanical support to the sphincter muscle and thus increase the closure forces exerted by the sphincter muscle on the urethra.

11. The method of claim 10 further comprising ablating the target volume so as to create a void therein and introducing the agent into the void.

12. The method of claim 10 further comprising supplying the agent to the tubular needle through an elongate probe member and heating the agent at a temperature above body temperature as it passes through the elongate probe member.

13. The method of claim 10 further comprising heating the agent after it has been introduced into the target volume of tissue.

14. The method of claim 10 wherein the advancing and introducing steps include advancing a plurality of tubular needles having respective free extremities with openings therein into tissue surrounding the urethra wall in a generally planar array so that the openings are in the target volumes and introducing the agent into the target volumes.

15. The method of claim 10 further comprising advancing an additional tubular needle having a free extremity with at least one opening therein into tissue surrounding the urethra wall which is spaced longitudinally along the urethra from the first named tissue simultaneously with the advancement of the first named tubular needle.

16. The method of claim 10 wherein the agent is crystallizable at body temperature.

17. The method of claim 16 wherein the agent is a side-chain crystallizable polymer.

* * * * *